(12) United States Patent
Storm

(10) Patent No.: US 8,027,717 B2
(45) Date of Patent: Sep. 27, 2011

(54) METHOD AND APPARATUS FOR MONITORING THE SEDATION LEVEL OF A SEDATED PATIENT

(75) Inventor: Hanne Storm, Oslo (NO)

(73) Assignee: Med Storm Innovation AS, Oslo (NO)

( * ) Notice: Subject to any disclaimer, the term of this patent is extended or adjusted under 35 U.S.C. 154(b) by 362 days.

(21) Appl. No.: 11/916,451

(22) PCT Filed: Jun. 8, 2006

(86) PCT No.: PCT/NO2006/000217
§ 371 (c)(1),
(2), (4) Date: Dec. 4, 2007

(87) PCT Pub. No.: WO2006/132545
PCT Pub. Date: Dec. 14, 2006

(65) Prior Publication Data
US 2008/0214908 A1   Sep. 4, 2008

(30) Foreign Application Priority Data
Jun. 10, 2005   (NO) .................... 20052833

(51) Int. Cl.
A61B 5/05 (2006.01)
A61B 5/00 (2006.01)
(52) U.S. Cl. ........................ 600/547; 600/306
(58) Field of Classification Search .......... 600/300, 600/547, 306
See application file for complete search history.

(56) References Cited

FOREIGN PATENT DOCUMENTS
EP 925758 6/1999
WO 03094726 11/2003

OTHER PUBLICATIONS
Storm, "Skin conductance correlates with perioperative stress", ACTA Anaesthesiol Scan 2002; 46:887-895.

Primary Examiner — Max Hindenburg
Assistant Examiner — Brian Szmal
(74) Attorney, Agent, or Firm — Christian Abel

(57) ABSTRACT
A method and an apparatus for monitoring the sedation level of a sedated patient during anaesthesia, in particular during a pre-surgical phase. The method comprises the steps of providing a skin conductance signal measured at an area of the patient's skin, calculating a derivative signal of said conductance signal with respect to time, and establishing said sedation level based on said derivative signal.

14 Claims, 3 Drawing Sheets

METHOD AND APPARATUS FOR MONITORING THE SEDATION LEVEL OF A SEDATED PATIENT

TECHNICAL FIELD

The invention relates in general to medical technology, and in particular to a method and an apparatus for monitoring patients during surgery and general anaesthesia. More specifically, the invention relates to a method and an apparatus for monitoring the sedation level of a sedated patient, in particular during a pre-surgical phase.

BACKGROUND OF THE INVENTION

During surgery it is very important to observe the patient's level of consciousness and awareness. Few reliable methods of observation exist today. In the field of medical technology there is a problem in producing physical measurements representing the activity in an individual's autonomous nervous system, i.e. in the part of the nervous system, which is beyond the control of the will.

Particularly, there is a special need to establish a state of a sufficiently deep sedation in the patient, in order to avoid administering more anaesthesia than necessary during surgery and general anaesthesia.

RELATED BACKGROUND ART

WO-03/94726 discloses a method and an apparatus for monitoring the autonomous nervous system of a sedated patient. In the method, a skin conductance signal is measured at an area of the patient's skin. Certain characteristics, including the average value of the skin conductance signal through a time interval and the number of fluctuation peaks through the interval, is calculated. Based on these characteristics, two output signals are established, indicating pain discomfort and awakening in the patient, respectively. The awakening signal is established based on the number of fluctuations and the average value through an interval.

SUMMARY OF THE INVENTION

An object of the present invention is to provide a method and an apparatus for monitoring a sedated patient, in particular a method and an apparatus for establishing a signal indicating the state of sedation in the patient, based on skin conductance measurements.

Another object of the present invention is to provide such a method and apparatus which provides more reliable output indications.

A special object of the invention is to provide such a method and an apparatus which indicates a state of a sufficiently deep sedation in the patient, in order to avoid administering more anaesthesia than necessary during surgery and general anaesthesia.

Another object of the present invention is to provide such a method and apparatus which do not rely on the calculating of the number of fluctuation peaks or average value of the skin conductance signal through any measurement interval.

The above and additional objects are obtained by a method and an apparatus as set forth in the appended independent claims.

Further advantages are achieved by the preferred embodiments set forth in the dependent claims.

BRIEF DESCRIPTION OF THE DRAWINGS

The invention will now be described in more detail with reference to the attached drawings, in which.

DETAILED DESCRIPTION OF THE INVENTION

Figure 1:
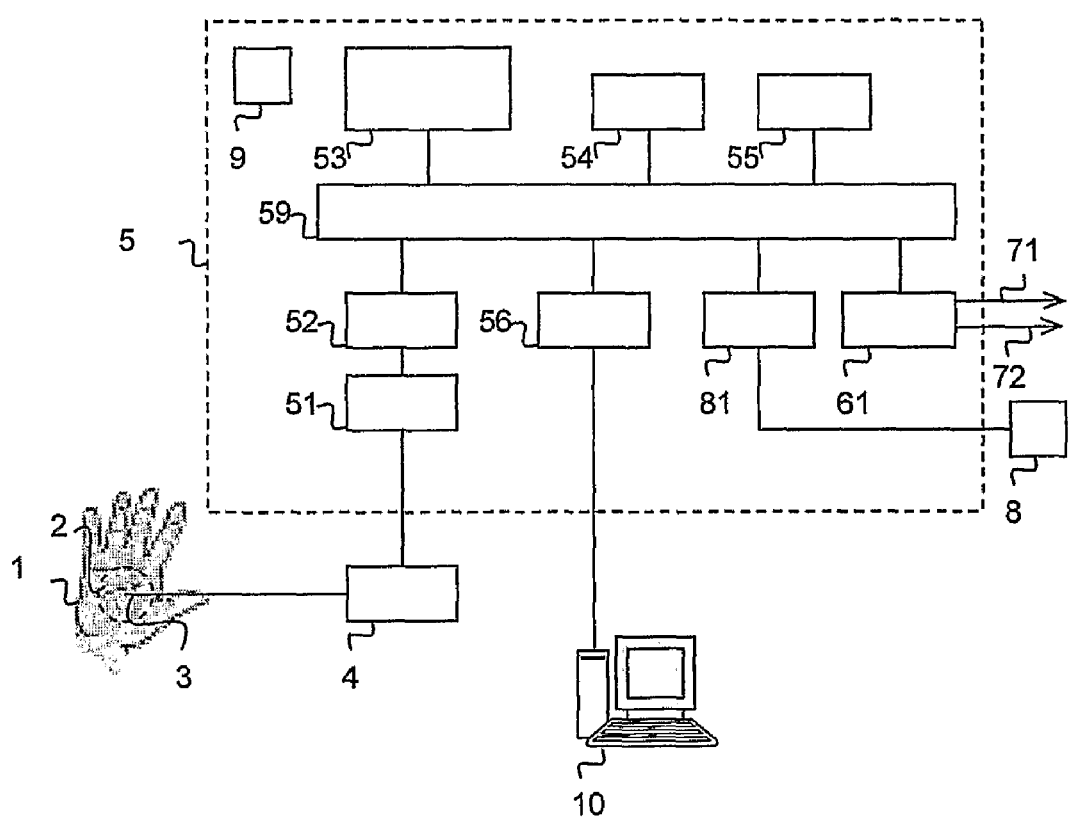
FIG. 1 is a block diagram for an apparatus according to the invention.

FIG. 1 illustrates a block diagram for a preferred embodiment of an apparatus according to the invention. On an area 2 of the skin on a body part 1 of the patient, sensor means 3 are placed for measuring the skin's conductance. The body part 1 is preferably a hand or a foot, and the area 2 of the skin on the body part 1 is preferably the palmar side of the hand (in the palm of the hand) or the plantar side of the foot (under the sole of the foot). The sensor means 3 comprise contact electrodes where at least two electrodes are placed on the skin area 2. In a preferred embodiment the sensor means 3 consist of three electrodes: a signal electrode, a measuring electrode and a reference voltage electrode, which ensures a constant application of voltage over the stratum corneum (the surface layer of the skin) under the measuring electrode. The measuring electrode and the signal electrode are preferably placed on the skin area 2. The reference voltage electrode may also be placed on the skin area 2, but it is preferably placed in a nearby location, suitable for the measuring arrangement concerned.

In a preferred embodiment an alternating current is used for measuring the skin's conductance. The alternating current advantageously has a frequency in the range of up to 1000 Hz, corresponding to the area where the skin's conductance is approximately linear. A frequency should be selected which ensures that the measuring signal is influenced to the least possible extent by interference from, e.g., the mains frequency. In a preferred embodiment the frequency is 88 Hz. A signal generator, operating at the specified frequency, applies a signal current to the signal electrode.

In the case of alternating current the conductance is identical to the real part of the complex admittance, and therefore not necessarily identical with the inverse value of the resistance. An advantage of using alternating current instead of direct current in conductance measurement is that by this means one avoids the invidious effect on the measurements of the skin's electrical polarizing properties.

The resulting current through the measuring electrode is conveyed to a measurement converter 4. This comprises a current to voltage converter, which in a preferred embodiment is a transresistance amplifier, but in its simplest form may be a resistance, which converts the current from the measuring electrode to a voltage.

The measurement converter further comprises a decomposition circuit, preferably in the form of a synchronous rectifier, which decomposes the complex admittance in a real part (the conductance) and an imaginary part (the susceptance). However, it is sufficient if the decomposition circuit only comprises means for deriving the conductance. The synchronous rectifier multiplies the measured voltage with the voltage from the signal generator. The two signals are in-phase. After multiplication, the result is according to the cosine (2u) equation, where the result is a DC component and one component at 2u frequency. In the preferred embodiment, this becomes 176 Hz. In the preferred embodiment, this synchronous rectifier is realized as an analog circuit with the required accuracy.

The measurement converter 4 may also comprise amplifier and filter circuits. In the preferred embodiment the measurement converter contains low-pass filters, both at the input and at the output. The object of the input low-pass filter is to attenuate high-frequency noise, for instance coming from other medical equipments, and also to serve as anti-aliasing filter to prevent high frequency components from being received by subsequent circuits for time discretization. The output low-pass filter shall attenuate the 2u components that result from the multiplication operation in the synchronous rectifier so that only the signal near DC is used for further processing.

By means of the choice of components and design details, moreover, the measurement converter is designed with a view to obtaining high sensitivity and a low noise level.

The control unit 5 comprises a time discretization unit 51 for time discretization of the signal from the measurement converter. The time discretization takes place at a sampling rate, which may advantageously be in the order of 20 to 200 samplings per second. The control unit further comprises an analog-digital converter 52, which converts measurement data to digital form. The choice of circuits for time discretization and analog-digital conversion implies technical decisions suitable for a person skilled in the art. In the preferred embodiment, time discretization is done in an integrated circuit, which combines oversampling, filtering and discretization.

The control unit may advantageously comprise additional analog and possibly also digital inputs (not illustrated), in addition to the input from the measurement converter 4. In this case the control unit 5 can either be equipped with a plurality of analog-digital converters 52, or it can employ various multiplexing techniques well-known to those skilled in the art in order to increase the number of analog inputs. These additional analog inputs may, for example, be arranged for additional electrodermal measurements, or for other physiological measurements which may advantageously be performed simultaneously or parallel with the electrodermal measurement, such as temperature, pulse, ECG, respiratory measurements, oxygen saturation measurements in the blood, or EEG (bispectral index).

The measurement converter 4 preferably includes a synchronous rectifier and a low pass filter; which converts the measured signal into a voltage. This voltage is further sent to control unit 5; which includes time discretization module 51 and analog-digital converter 52, which converts measurement data to digital form. The choice of circuits for time discretization and analog-digital conversion implies technical decisions suitable for a person skilled in the art. In the preferred embodiment, time discretization is done in an integrated circuit, which combines oversampling, filtering and discretization.

The control unit 5 also comprises a processing unit 53 for processing the digitized measurement data, storage means in the form of at least one store for storing data and programs, illustrated as a non-volatile memory 54 and a random access memory 55. The control unit 5 further comprises an interface circuit 61, which provides an output signal 71. An auxiliary output signal 72 is also shown. Preferably, the control unit 5 further comprises a further interface circuit 81, which is further connected to display unit 8. The control unit 5 may also advantageously comprise a communication port 56 for digital communication with an external unit, such as a personal computer 10. Such communication is well-suited for loading or altering the program which is kept stored in the memory 54, 55 in the control unit, or for adding or altering other data which are kept stored in the memory 54, 55 in the control unit. Such communication is also well suited for read-out of data from the memory 54, 55 in the apparatus, thus enabling them to be transferred to the external computer 10 for further, subsequent analysis or storage. A communication port 56 in the control unit will be advantageously designed in accordance with requirements for equipment safety for patients, as described in more detail below.

In a preferred embodiment the non-volatile memory 54 comprises a read-only storage in the form of programmable ROM circuits, containing at least a program code and permanent data, and the random access memory 55 comprises a read and write storage in the form of RAM circuits, for storage of measurement data and other provisional data.

The control unit 5 also comprises an oscillator (not shown), which delivers a clock signal for controlling the processing unit 53. The processing unit 53 also contains timing means (not shown) in order to provide an expression of the current time, for use in the analysis of the measurements. Such timing means are well-known to those skilled in the art, and are often included in micro controllers or processor systems which the skilled person will find suitable for use with the present invention.

The control unit 5 may be realized as a microprocessor-based unit with connected input, output, memory and other peripheral circuits, or it may be realized as a micro controller unit where some or all of the connected circuits are integrated. The time discretization unit 51 and/or analog-digital converter 52 may also be included in such a unit. The choice of a suitable form of control unit 5 involves decisions, which are suitable for a person skilled in the art.

An alternative solution is to realize the control unit as a digital signal processor (DSP).

Several structural hardware components of the present invention may be identical to those used in WO-03/94726. However, the method or process performed by the control unit 5, in order to analyze the skin conductance signal, is distinctive and substantially different from the method/process disclosed in WO-03/94726.

The data processing unit 53 is arranged for analysing the measured and digitized signal provided by the A/D converter 52. The signal is analysed in order to extract different types of information.

The control unit 5 is arranged to read time-discrete and quantized measurements for the skin conductance from the measurement converter 4, preferably by means of an executable program code, which is stored in the non-volatile memory 54 and which is executed by the processing unit 53. It is further arranged to enable measurements to be stored in the read and write memory 55. By means of the program code, the control unit 5 is further arranged to analyze the measurements in real time, i.e. simultaneously or parallel with the performance of the measurements.

In this context, simultaneously or parallel should be understood to mean simultaneously or parallel for practical purposes, viewed in connection with the time constants which are in the nature of the measurements. This means that input, storage and analysis can be undertaken in separate time intervals, but in this case these time intervals, and the time between them, are so short that the individual actions appear to occur concurrently.

The processing unit 53, the memories 54, 55, the analog/digital converter 52, the communication port 56, the interface circuit 81 and the interface circuit 61 are all connected to a bus unit 59. The detailed construction of such bus architecture for the design of a microprocessor-based instrument is regarded as well-known for a person skilled in the art.

The interface circuit 61 is a digital port circuit, which derives output signals 71, 72 from the processing unit 53 via the bus unit 59 when the interface circuit 61 is addressed by the program code executed by the processing unit 53.

The output signal 71 indicates the sedation level in the patient. Preferably, the output signal 71 indicates that the analysis of the skin conductance measurement has detected that the patient has reached a sufficiently deep sedation level.

In a preferred embodiment the display means 8 consists of a screen for graphic visualization of the conductance signal, and a digital display for displaying the frequency and amplitude of the measured signal fluctuations. The display units are preferably of a type whose power consumption is low, such as an LCD screen and LCD display. The display means may be separate or integrated in one and the same unit.

The apparatus further comprises a power supply unit 9 for supplying operating power to the various parts of the apparatus. The power supply may be a battery or a mains supply of a known type.

The apparatus may advantageously be adapted to suit the requirements regarding hospital equipment, which ensures patient safety. Such safety requirements are relatively easy to fulfill if the apparatus is battery-operated. If, on the other hand, the apparatus is mains operated, the power supply shall meet special requirements, or requirements are made regarding a galvanic partition between parts of the apparatus (for example, battery operated), which are safe for the patient and parts of the apparatus, which are unsafe for the patient. If the apparatus has to be connected to external equipment, which is mains operated and unsafe for the patient, the connection between the apparatus, which is safe for the patient and the unsafe external equipment requires to be galvanically separated. Galvanic separation of this kind can advantageously be achieved by means of an optical partition. Safety requirements for equipment close to the patient and solutions for fulfilling such requirements in an apparatus like that in the present invention are well-known to those skilled in the art.

Figure 2:
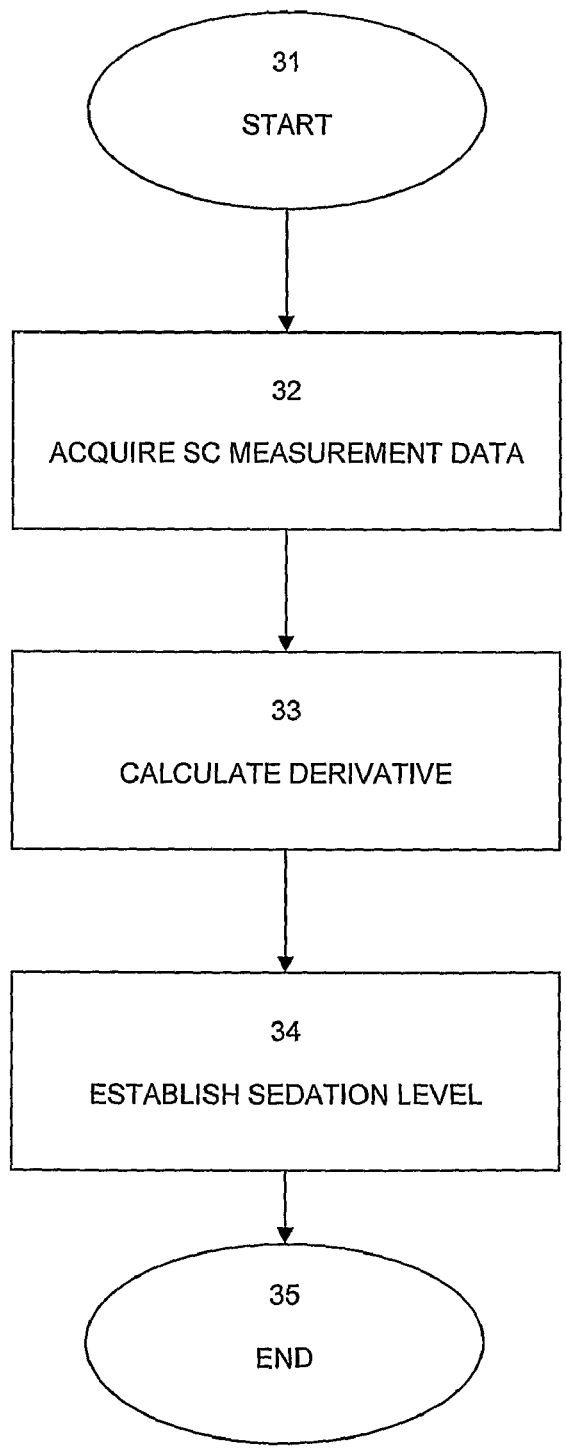
FIG. 2 is a flow chart illustrating a method according to the invention.

FIG. 2 illustrates a flow chart for a method for monitoring the sedation level of a sedated patient. The method is particularly used for monitoring the sedation level of the sedated patient during anaesthesia, and specifically, for monitoring the sedation level during a pre-surgical phase of the anaesthesia period.

The method starts at reference 31.

Next, in the acquiring step 32, a skin conductance signal or EDR (electrodermal response) signal is measured at the area 2 of the patient's skin, time-quantized and converted to digital form using the equipment described with reference to FIG. 1. A time-series of a certain duration, typically a period of at least 20 seconds, containing skin conductance data, is acquired during this step. With a sampling rate of 20-200 samples per second, the time-series may contain 400-4000 samples, respectively. The data is stored in a portion of the memory 55.

Advantageously, the acquiring step 32 also comprises a prefiltering process, wherein the measured data are filtered in order to remove high frequency noise, and irrelevant anomalies such as peaks or spikes caused by interference or measurement errors.

Next, in the derivative calculation step 33, a derivative signal of said conductance signal with respect to time is calculated by the processing unit 53. The calculating step advantageously comprises the following substeps:

First, to select a first skin conductance value at the start point of an interval, next, to select a second skin conductance value at the end point of the interval, and then calculating the derivative signal as the difference between said first and the second skin conductance values divided by the duration of the interval.

The duration of the interval is advantageously between 10 seconds and 30 seconds. More preferably the interval is between 15 seconds and 25 seconds. Most preferably the interval is about 20 seconds.

The calculated derivative signal is also stored in a portion of the memory 55.

Next, in step 34, a sedation level is established based on the derivative signal calculated in step 33.

Advantageously, the establishing step 34 comprises applying a non-linear transformation between the derivative signal calculated in step 33 the output sedation level. The transformation is preferably a discretization function, wherein said transformation is arranged for mapping a range of derivative signal values to a certain level in the OAAS scale.

The transformation is advantageously implemented as a series of comparison processing steps operating in accordance with limit values stored in a table in a portion of the memory 54.

The Observer's assessment of anaesthesia and sedation (OAAS) scale is well known in the art, used for assessing the hypnotic state of patients. The levels are given below:

Level 5: Patient is awake, eyes are open, and patient replies and responses readily to spoken commands.

Level 4: Patient is sedated, he or she responses to spoken commands such as 'squeeze my hand', but has mild ptosis, drowsiness.

Level 3: Patient responses only to loud spoken commands. The eyelid reflex is still present.

Level 2: Patient does not response to spoken commands. The eyelid reflex is not present.

Level 1: Patient does not response with movement to TOF stimulation (50 mA). No muscle relaxants are assumed.

Level 0: Patient does not response with movement to tetanic (50 mA) stimulation of the ulnar nerve. No muscle relaxants are assumed.

The establishing step 34 advantageously comprises to determine if the derivative signal value is in the range [−0.04 µS/s, −0.00 µS/s], and if so, to set the sedation level to an OAAS level of 4 or less.

The establishing step 34 advantageously comprises to determine if the derivative signal value is in the range [−0.04 µS/s, −0.02 µS/s], and if so, to set the sedation level to an OAAS level of 4 or 3.

The establishing step 34 advantageously comprises to determine if the derivative signal value is in the range [−0.02 µS/s, −0.00 µS/s], and if so, to set the sedation level to an OAAS level of 3 or 2.

The establishing step 34 advantageously comprises to determine if the derivative signal value is substantially 0.02 µS/s, and if so, to set the sedation level to an OAAS level of 2 or less.

Advantageous characteristics of the function between the derivative signal and the sedation level are given in table 1 below:

TABLE 1

Sedation level vs. derivative SC signal

| Derivative of SC signal, range (µS/s) | Discretizated sedation level output (OAAS level) |
|---|---|
| −0.03 +/− 0.01 | OAAS 4-3 |
| −0.01 +/− 0.01 | OAAS 3-2 |
| 0 | OAAS <2 |

Advantageously, the step 34 of establishing said sedation level further comprises generating an output signal which indicates said sedation level. The signal may be a digital signal which is displayed on the display 8, and/or output as the output signal 71 to an external equipment.

The invention thus relates both to the method described with reference to FIG. 2, and to an apparatus for monitoring the sedation level of a sedated patient during anaesthesia, in particular during a pre-surgical phase. Structurally, the apparatus may be as substantially described with reference to FIG. 1. The apparatus comprises measurement equipment for providing a skin conductance signal measured at an area of the patient's skin, and a control unit which is arranged for performing a method substantially corresponding to the method illustrated in FIG. 2.

After the completion of the establishing step 34, the process may be terminated as illustrated by the terminating step 35. Alternatively, the process may be repeated, using another measurement acquiring period and/or another period for calculating the derivative signal.

Figure 3:
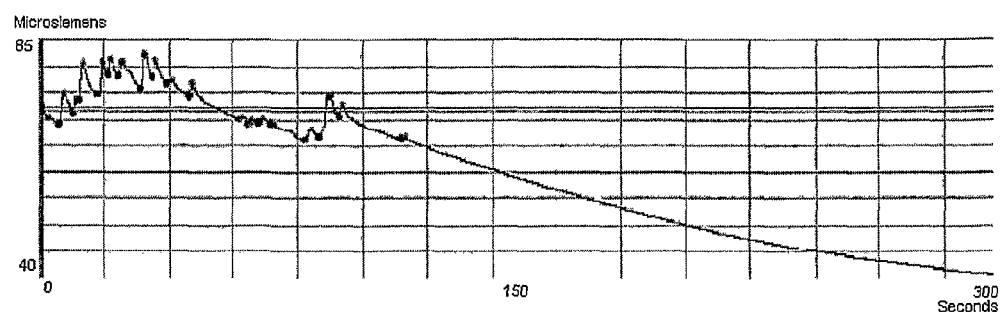
FIG. 3 is a measurement plot of a time series of an acquired skin conductance signal.

FIG. 3 is a measurement plot of a time series of an acquired skin conductance signal during a pre-surgical anaesthesia phase. The signal is measured in the palm of a human patient, in the period of 0 to 300 seconds after propofol infusion.

As shown in FIG. 3, the SC signal decreases with time, i.e. as the sedation level of the patient changes from awake (OAAS level 5 at 0 seconds) to deeper sedation (at about 300 seconds). The derivative of the signal is calculated as the relative difference (i.e. divided by the duration of the interval) between the start SC value and the end SC value over a period of typically 20 seconds. As will be appreciated, the derivative signal is negative in most of the pre-surgical anaesthesia phase, indicating that the sedation level increases (i.e., the OAAS level is reduced). Moreover an increase in the derivate is expected if the OAAS level is increased.

The skilled person will realize that the above description has been presented as an detailed example of a particular embodiment, and that the principles of the invention may be put into effect in other ways as well. As an example, the skilled person will realize that skin resistance may be measured instead of skin conductance, provided that the inverse nature of these variables is taken into account.

When the term "patient" is used throughout the specification and claims, is should be appreciated that although the present invention is primarily directed towards the monitoring of human beings, the invention has also been proven to be applicable for monitoring animals, in particular mammals. Consequently, the term "patient" should be interpreted as covering both human and animal patients.

The invention claimed is:

1. Method for monitoring the sedation level of a sedated patient during anaesthesia, the method comprising the steps of:
   providing, from a skin conductance measuring equipment, a skin conductance signal measured at an area of the patient's skin,
   calculating, by a processing unit in an apparatus for monitoring the sedation level of the sedated patient, a derivative signal of said conductance signal with respect to time,
   establishing, by the processing unit, said sedation level based on said derivative signal, including applying a discretization function mapping a range of derivative signal values to a certain level in a sedation level scale,
   wherein a derivative signal value in the range [−0.02 μS/s, −0.00 μS/s] corresponds to a sedation level in the sedation level scale indicating that the patient does not respond to spoken commands or responses only to loud spoken commands.

2. Method according to claim 1,
   wherein said step of calculating said derivative signal further comprises
   selecting a first skin conductance value at the start point of an interval,
   selecting a second skin conductance value at the end point of said interval, and
   calculating the derivative signal as the difference between said first and the second skin conductance values divided by the duration of said interval.

3. Method according to claim 2,
   wherein said duration of said interval is between 10 seconds and 30 seconds.

4. Method according to claim 3, wherein said duration is between 15 seconds and 25 seconds.

5. Method according to claim 4, wherein said duration is 20 seconds.

6. Method according to claim 1,
   wherein said step of establishing said sedation level comprises
   generating an output signal which indicates said sedation level.

7. Method according to claim 1,
   wherein said step of providing a skin conductance signal comprises
   measuring the skin conductance on the palmar side of the patient's hand.

8. Method according to claim 1,
   wherein said step of providing a skin conductance signal comprises
   measuring the skin conductance on the plantar side of the patient's foot.

9. Method according to claim 1,
   wherein said step of providing a skin conductance signal comprises
   measuring the skin conductance using an alternating current with a frequency in the range up to 1000 Hz.

10. Method according to claim 1,
    wherein said patient is a human.

11. Method according to claim 1,
    wherein said patient is an animal.

12. Method according to claim 1, wherein said sedation level is the OAAS scale.

13. Method according to claim 12, wherein said level indicating that the patient does not respond to spoken commands or responses only to loud spoken commands corresponds to an OAAS level of 3 or 2.

14. Apparatus for monitoring the sedation level of a sedated patient during anaesthesia, in particular during a pre-surgical phase, the apparatus comprising:
    measurement equipment for providing a skin conductance signal measured at an area of the patient's skin, and
    a control unit, arranged to perform the following steps:
    calculating a derivative signal of said conductance signal with respect to time,
    establishing said sedation level based on said derivative signal, including applying a discretization function mapping a range of derivative signal values to a certain level in a sedation level scale,
    wherein a derivative signal value in the range [−0.02 μS/s, −0.00 μS/s] corresponds to a sedation level in the sedation level scale indicating that the patient does not respond to spoken commands or responses only to loud spoken commands.

* * * * *